US008293784B2

(12) United States Patent
Rudolph et al.

(10) Patent No.: US 8,293,784 B2
(45) Date of Patent: Oct. 23, 2012

(54) α-AMINO ACID DERIVATIVES FOR IMPROVING SOLUBILITY

(75) Inventors: Thomas Rudolph, Darmstadt (DE); Herwig Buchholz, Frankfurt am Main (DE); Michaela Oberle, Rodgau (DE)

(73) Assignee: Merck Patent GmbH, Darmstadt (DE)

( * ) Notice: Subject to any disclaimer, the term of this patent is extended or adjusted under 35 U.S.C. 154(b) by 222 days.

(21) Appl. No.: 12/745,143

(22) PCT Filed: Nov. 27, 2008

(86) PCT No.: PCT/EP2008/010045
§ 371 (c)(1),
(2), (4) Date: May 27, 2010

(87) PCT Pub. No.: WO2009/068275
PCT Pub. Date: Jun. 4, 2009

(65) Prior Publication Data
US 2011/0039924 A1 Feb. 17, 2011

(30) Foreign Application Priority Data

Nov. 29, 2007 (DE) .................. 10 2007 057 543

(51) Int. Cl.
*A61K 31/352* (2006.01)
*A61K 31/195* (2006.01)
*A61K 47/18* (2006.01)
*A61K 47/12* (2006.01)

(52) U.S. Cl. ......... 514/456; 514/561; 514/784; 514/788

(58) Field of Classification Search .................. 514/456, 514/561, 784, 788
See application file for complete search history.

(56) References Cited

U.S. PATENT DOCUMENTS

| 4,980,165 | A | 12/1990 | Isaacs |
| 5,496,565 | A | 3/1996 | Heinze et al. |
| 6,238,650 | B1 | 5/2001 | Lapidot et al. |
| 6,242,099 | B1 | 6/2001 | Grandmontagne et al. |
| 6,303,149 | B1 | 10/2001 | Magdassi et al. |
| 2003/0114324 | A1 | 6/2003 | Lange |
| 2004/0043940 | A1 | 3/2004 | Bunger |
| 2004/0091433 | A1 | 5/2004 | Buchholz et al. |
| 2004/0220137 | A1 | 11/2004 | Sauermann |
| 2006/0029563 | A1 | 2/2006 | Thorel |
| 2007/0027223 | A1 | 2/2007 | Bruchert |
| 2007/0155695 | A1 | 7/2007 | Wirth |

FOREIGN PATENT DOCUMENTS

| CH | 685561 | 8/1995 |
| DE | 41 16 123 A1 | 11/1992 |
| DE | 43 08 282 A1 | 9/1994 |
| DE | 101 33 202 A1 | 1/2003 |
| DE | 102 32 595 A1 | 2/2004 |
| EP | 1407758 | 4/2004 |
| WO | WO 00/09652 A2 | 2/2000 |
| WO | WO 00/71084 A1 | 11/2000 |
| WO | WO 00/72806 A2 | 12/2000 |

*Primary Examiner* — Raymond Henley, III
(74) *Attorney, Agent, or Firm* — Millen, White, Zelano, Branigan, P.C.

(57) ABSTRACT

The invention relates to the use of α-amino acid derivatives for improving the solubility of sparingly soluble substances in water or aqueous solutions, and to mixtures and preferred compositions.

24 Claims, No Drawings

α-AMINO ACID DERIVATIVES FOR IMPROVING SOLUBILITY

The present invention relates to the use of α-amino acid derivatives for improving the solubility of sparingly soluble substances in water or aqueous solutions, and to mixtures and preferred compositions.

Active compounds are substances which—occurring or added in relatively small amounts—are able to develop a large physiological action. They have now become indispensable in our everyday lives and play an important role, for example, both in beauty care and in medical treatment and the uptake of nutrition.

It is known that adequate solubility of active compounds in non-solid compositions, such as, for example, emulsions, is of major importance with respect to the action potential of the substance and with respect to the pharmaceutical acceptance of the composition.

For a number of sparingly soluble components, it is known that it is only with difficulty that they achieve adequate solubility in the composition without recrystallisation effects.

It is known that, in particular, the use of natural products or nature-identical products, such as, for example, bioflavonoids, chromones, chromanones, coumarines and coumaranones, may be considerably limited by their poor solubility. Furthermore, inadequate solubility may also represent a considerable deficiency for numerous synthetic components. Examples thereof which may be mentioned are selected cosmetic active compounds, such as, for example, UV filters, antioxidants, self-tanning/skin-lightening active compounds, antiageing active compounds, but also pharmacological active compounds.

It is therefore desirable to develop compositions which overcome this deficiency. At the same time, alternative deficiencies should not be produced, as is the case, for example, through the use of undesired secondary components, such as, for example, solubilisers.

A further difficulty in the preparation of cosmetics consists in that active compounds which are to be incorporated into cosmetic compositions frequently do not have adequate solubility in the acidic pH range.

For example, Eusolex® 232 (phenylbenzimidazolesulfonic acid, 2-phenylbenzimidazole-5-sulfonic acid, PBSA) must be rendered slightly alkaline for use in cosmetic products in order to achieve adequate solubility. The requisite alkaline pH of the formulation of pH 7 to 8 is disadvantageous here. By contrast, acidic cosmetics are preferred for reasons of tolerability and the naturally acidic pH of the skin. However, it has to date not been possible to for many active compounds, for example PBSA, to be used in the acidic range since recrystallisation of the sulfonic acid occurs here. The ideal value of a cosmetic formulation is pH 5.5 and thus corresponds to the natural pH of the skin.

In general, the comments for PBSA also apply generally to organic acids which are to be formulated in this way. Examples of organic acids are preservatives in the form of the free acid or also pharmacological active compounds in the form of the free acid.

A further disadvantage of alkaline formulations is, in addition, that oxidation-sensitive substances, such as, for example, phenolic substances or vitamins, such as, for example, vitamin C and vitamin C derivatives (as disclosed, for example, in WO2008017346), and self-tanning substances, such as dihydroxyacetone, can easily be oxidised, while, as is known, oxidation stability is generated with falling pH.

There is therefore a demand for skin-tolerated solubilisers which are also suitable for use in skin-care, cosmetic and dermatological compositions.

The object of the present invention is therefore to provide compounds whose use improves the solubility of substances which are sparingly soluble in water if the pH of the solution is less than pH 7.

Surprisingly, it has been found that derivatives of α-amino acids are highly suitable for increasing the solubility of sparingly soluble substances, as defined above.

The present invention therefore relates firstly to the use of at least one α-amino acid derivative, a salt or hydrate thereof for improving the solubility of one or more sparingly soluble substances in water or aqueous solutions. The α-nitrogen atom of the at least one α-amino acid derivative here is quaternary, tertiary or secondary.

For the purposes of this invention, sparingly soluble substances are regarded as being, in particular, substances whose solubility in water at a temperature between 20° C. and 25° C. is less than 1% by weight if the pH of the solution is less than pH 7.

In the use according to the invention, it is therefore preferred to improve the solubility of a substance whose solubility in water in the absence of the α-amino acid derivative at a temperature of between 20° C. and 25° C. and at a pH of the composition of between 3 and 6.5 is less than 1% by weight.

Advantages of the use according to the invention are, in particular, the good skin tolerability and the fact that the use according to the invention of the α-amino acid derivative enables active compounds which have adequate solubility only in the alkaline region also to be used in acidic or neutral cosmetic and dermatological compositions.

In addition, it is possible by means of the present invention on the one hand to dissolve previously sparingly soluble active compounds at an acidic pH and thereby additionally to enable combination with substances which are protected against oxidation in acidic media, but would otherwise be unstable under alkaline conditions and thus could not be combined with the active compound which is sparingly soluble in acidic media.

For example, the present invention now enables the substance phenylbenzimidazolesulfonic acid (PBSA, Eusolex® 232), which originally could only be dissolved in neutral to alkaline media, to be combined with oxidation-sensitive substances, such as dihydroxyacetone or vitamin C, in acidic media. As is known, dihydroxyacetone and vitamin C would be unstable in alkaline media. In acidic media, by contrast, PBSA would crystallise out after conventional procedures.

For the purposes of this invention, the term adequate solubility describes the property of a substance of not crystallising out during product-specific storage. Depending on the application, adequate solubility is regarded, in particular, as a solubility which ensures good efficacy at the same time as storage stability.

Good efficacies are achieved if sufficient active compound can be dissolved in the formulation and also remains dissolved during storage, i.e. in this case does not crystallise out again.

In the use according to the invention, the at least one α-amino acid derivative used is preferably a non-amphoteric betaine, 2-pyrrolidone-5-carboxylic acid and/or a derivative of formiminoglycine.

The term betaine very generally encompasses all compounds which contain a quaternary ammonium group and an acid radical. Without restricting generality, the non-amphoteric betaine used in accordance with the invention is particularly preferably trimethylglycine.

The further α-amino acid derivative used is particularly preferably 2-pyrrolidone-5-carboxylic acid:

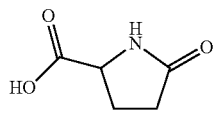

Without restricting generality, the derivative of formiminoglycine used in accordance with the invention is particularly preferably one or more of the following compounds:

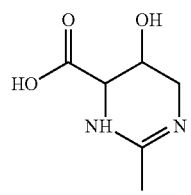 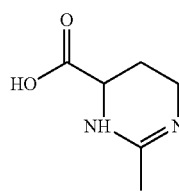 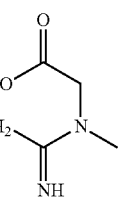

ectoine    hydroxyectoine    creatine

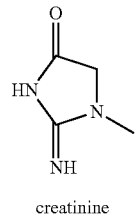

creatinine

The formiminoglycine used in accordance with the invention is very particularly preferably ectoine or creatinine.

The α-amino acid derivative used in accordance with the invention is particularly preferably a derivative of formiminoglycine.

The α-amino acid derivative used for improving the solubility of one or more sparingly soluble substances in water or aqueous solutions is very particularly preferably creatinine.

All α-amino acid derivatives can also be used in accordance with the invention in the form of their salts or hydrates, for example creatine hydrate.

In accordance with the invention, the solubility of a sparingly soluble substance selected from the group of chromones, chromanones, flavonoids and organic acids, for example preservatives in the form of the free acid, pharmacological active compounds in the form of the free acid, cosmetic active compounds in the form of the free acid, is preferably improved. Particularly preferred organic acids are aromatic monosulfonic acids.

Chromone derivatives are preferably taken to mean certain chromenone derivatives which are suitable as active compounds for the preventative treatment of human skin and human hair against ageing processes and damaging environmental influences. At the same time, they exhibit a low irritation potential for the skin, have a positive effect on the binding of water in the skin, maintain or increase the elasticity of the skin and thus promote smoothing of the skin.

Without restricting generality, the sparingly soluble chromenone whose solubility is improved in accordance with the invention is particularly preferably a compound of the general formula (I)

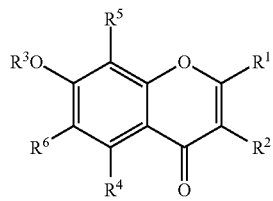

where
$R^1$ and $R^2$ may be identical or different and stand for H, straight-chain or branched $C_1$- to $C_{20}$-alkyl groups or straight-chain or branched $C_1$- to $C_{20}$-hydroxyalkyl groups,
$R^3$ stands for H or a straight-chain or branched $C_1$- to $C_{20}$-alkyl group,
$R^4$ stands for H or $OR^7$,
$R^5$ and $R^6$ may be identical or different and stand for H, OH or straight-chain or branched $C_3$- to $C_{20}$-alkenyl groups,
$R^7$ stands for H or a straight-chain or branched $C_1$- to $C_{20}$-alkyl group,
where at least two of the substituents $R^1$, $R^2$, $R^4$ to $R^6$ are different from H.

Of the chromone derivatives of the formula (I), 5,7-dihydroxy-2-methylchromone is particularly preferred.

Chromanone derivatives are preferably taken to mean certain chromanone derivatives which are suitable as active compounds for the care, preservation or improvement of the general condition of the skin or hair and for prophylaxis against time- and/or light-induced ageing processes of the human skin or human hair and for the prophylaxis and/or treatment of skin diseases. At the same time, they exhibit a low irritation potential for the skin, have a positive effect on the binding of water in the skin, maintain or increase the elasticity of the skin and thus promote smoothing of the skin.

Without restricting generality, the sparingly soluble substance whose solubility is improved in accordance with the invention is particularly preferably a compound of the general formula (II)

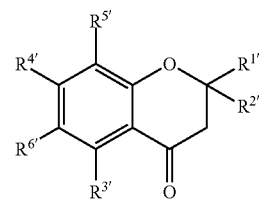

where
$R^{1'}$ and $R^{2'}$ may be identical or different and are selected from H,
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups,
$C_3$- to $C_{10}$-cycloalkyl groups and/or $C_3$- to $C_{12}$-cycloalkenyl groups, where each of the rings may also be bridged by —$(CH_2)_n$— groups, where n=1 to 3,
or $R^{1'}$ and $R^{2'}$ are linked by $(CH_2)_o$, where o stands for 0, 1, 2, 3, 4, 5 or 6,
$R^{3'}$, $R^{4'}$ and $R^{5'}$ are each selected, independently of one another, from
H, OH,
straight-chain or branched $C_1$- to $C_{20}$-alkoxy groups,
straight-chain or branched $C_1$- to $C_{20}$-acyloxy groups,
straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, and $R^{6'}$ stands for H, OH, COOH, COCH$_3$, a straight-chain or branched $C_1$- to $C_{20}$-alkyl group, a straight-chain or branched $C_3$- to $C_{20}$-alkenyl group, a straight-chain or branched $C_1$- to $C_{20}$-hydroxyalkyl group, a straight-chain or branched $C_1$- to $C_{20}$-alkoxy group, a straight-chain or branched $C_1$- to $C_{20}$-alkyl group, a straight-chain or branched $C_1$- to $C_{20}$-alkoxycarbonyl group or a straight-chain or branched $C_1$- to $C_{20}$-acyloxy group.

Of the chroman-4-one derivatives of the formula (II), particular preference is given to 5,7-dihydroxy-2,2-dimethylchroman-4-one or 6-hydroxy-2,2-dimethylchroman-4-one, very particularly preferably 6-hydroxy-2,2-dimethylchroman-4-one.

The proportion of one or more compounds selected from chromone or chromanone derivatives in a composition is preferably from 0.001% by weight to 5% by weight, particularly preferably from 0.01% by weight to 2% by weight, based on the composition as a whole.

In accordance with the invention, flavonoids are taken to mean the glycosides of flavanones, flavones, 3-hydroxyflavones (=flavonols), aurones, isoflavones and rotenoids [Römpp Chemie Lexikon [Römpp's Lexicon of Chemistry], Volume 9, 1993]. For the purposes of the present invention, however, they are also taken to mean the aglycones, i.e. the sugar-free constituents, and the derivatives of the flavonoids and aglycones. Furthermore, the term flavonoid is also taken to mean anthocyanidine (cyanidine) for the purposes of the present invention.

The use of flavonoids, in particular in cosmetics and pharmacy, is known per se. Flavonoids are generally sparingly soluble compounds, with the exception of, for example, troxerutin and α-glucosylrutin.

Without restricting generality, the sparingly soluble substance whose solubility is improved in accordance with the invention is preferably isoquercetin or a compound of the general formula (III)

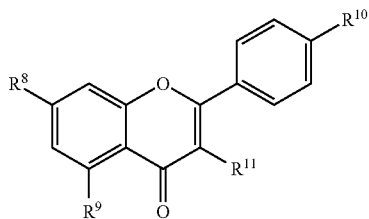

where $R^8$, $R^9$ and $R^{10}$ may be identical or different and each stand, independently of one another, for OH, CH$_3$COO, alkoxy or monoglycoside radicals, where the alkoxy radicals may be branched or unbranched and can have 1 to 8 C atoms, $R^{11}$ is a mono- or diglycoside radical, where in each case

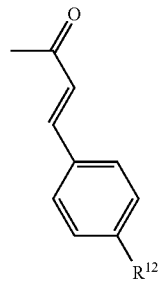

is bonded to this glycoside radical via an —O— group, $R^{12}$ has the meaning of the radicals $R^8$ to $R^{10}$, and where one or more hydrogen atoms in the OH groups of the glycoside radical(s) may each also be replaced, independently of one another, by acetyl or by alkyl radicals having 1 to 8 C atoms.

Of the compounds of the formula (III), tiliroside is particularly preferred.

The at least one flavonoid, as described above, is preferably employed for the use according to the invention in corresponding formulations in a total amount of 0.01% by weight to 10% by weight, more preferably in an amount of 0.1% by weight to 5% by weight.

Suitable preservatives in the form of the free acid are benzoic acid, benzylic acid, formic acid, propionic acid, salicylic acid and sorbic acid. The solubilisation of the α-amino acid derivative greatly improves, in particular, the preserving action. Creatinine enables the preservative in the form of the free acid also to be dissolved in the compositions having skin-similar pH.

Aromatic monosulfonic acids are active compounds which are suitable, inter alia, as UV filters, in particular in cosmetics and pharmacy. Their use in cosmetic and dermatological compositions is known.

Without restricting generality, the aromatic monosulfonic acid whose solubility is improved in accordance with the invention is particularly preferably a UV filter which is only water-soluble in alkaline media, selected from the group of 2-arylbenzimidazole-5-sulfonic acids, 2-hydroxy-4-methoxybenzophenone-5-sulfonic acid and sulfonic acid derivatives of 3-benzylidenecamphor.

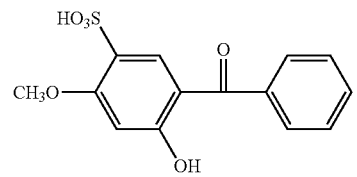

2-Hydroxy-4-methoxybenzophenone-5-sulfonic acid.

Arylbenzimidazolesulfonic acids preferably conform, for example, to the general formula (IV)

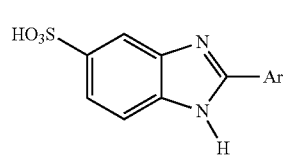

where Ar stands for phenyl which is unsubstituted or substituted by one or more $C_1$- to $C_6$-alkyl or -alkoxy groups.

Of the compounds of the formula IV, 2-phenylbenzimidazole-5-sulfonic acid is particularly preferred.

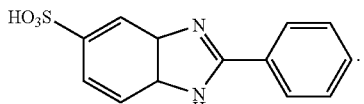

2-Phenylbenzimidazole-5-sulfonic acid

Monosulfonic acid derivatives of 3-benzylidenecamphor are, for example, 4-(2-oxo-3-bornylidenemethyl)benzenesulfonic acid or 2-methyl-5-(oxo-3-bornylidenemethyl)benzenesulfonic acid.

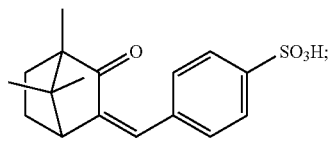

4-(2-Oxo-3-bornylidenemethyl) benzenesulfonic acid

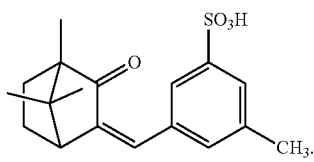

3-Methyl-5-[4,7,7-trimethyl-3-oxobicyclo[2.2.1]hept-(2Z)-ylidenemethyl] benzenesulfonic acid Without restricting generality, the solubility of, for example, tiliroside, 5,7-dihydroxy-2-methylchromen-4-one or Eusolex® 232 (2-phenylbenzimidazole-5-sulfonic acid) in water or an aqueous solution is improved by the use of 2-pyrrolidone-5-carboxylic acid, ectoine, hydroxyectoine, creatine or creatinine.

2-Phenylbenzimidazole-5-sulfonic acid is particularly preferably used as sparingly soluble substance in water or aqueous solutions.

A preferred aqueous solution is, for example, a mixture of water and an alcohol, such as methanol, ethanol or propanol, particularly preferably ethanol. The alcohol to water weight ratio is preferably between 10:1 and 1:100, particularly preferably between 5:1 and 1:50. However, embodiments of aqueous solutions which comprise no alcohol are also preferred. In aqueous solutions of this type, the solubility of aromatic monosulfonic acids, in particular of 2-phenylbenzimidazole-5-sulfonic acid, is particularly preferably improved.

An advantage of the particularly preferred combination of creatinine with PBSA is the improvement in the binding of the UV filter PBSA to hair for improved hair care or hair protection. Furthermore, effective UV protection of hair dyes or of dyed hair against UV-induced colour change can be achieved in this way.

A further advantage of the particularly preferred combination of creatinine with PBSA is the water resistance of compositions comprising this combination. Analogously to the hair-care effect described, creatinine increases the skin substantivity of PBSA. This results in improved water resistance of compositions, in particular of sunscreen products. The use of this preferred combination of creatinine with PBSA also improves the sweat or moisture resistance of PBSA-containing products.

The present invention furthermore relates to compositions, preferably cosmetic compositions, pharmaceutical compositions, medical products or foods, which comprise at least one α-amino acid derivative and at least one sparingly soluble substance as defined above, where the proportion of the α-amino acid derivative in percent by weight is greater than the proportion of the sparingly soluble substance in percent by weight, based on the composition.

In an embodiment, preference is given to compositions in which the α-amino acid derivative is selected from 2-pyrrolidone-5-carboxylic acid, creatinine, creatine, ectoine and hydroxyectoine; creatinine is very particularly preferably selected. Preference is furthermore given to compositions in which the sparingly soluble substance is an aromatic monosulfonic acid. Very particularly preferred compositions comprise creatinine and PBSA.

In a preferred embodiment of the composition according to the invention, the at least one α-amino acid derivative is present in an amount of 0.05% by weight to 20% by weight, preferably in an amount of 0.5% by weight to 10% by weight and particularly preferably in an amount of 1% by weight to 5% by weight.

In a further preferred embodiment of a composition, the at least one α-amino acid derivative and the at least one aromatic monosulfonic acid are present in a percent by weight ratio of 10:1 to 1.1:1, preferably 5:1 to 1.5:1, very particularly preferably 3:1 to 2:1.

An advantage of this composition according to the invention is that the pH of the aqueous phase of the composition is less than 7, preferably less than 6.5. In other words, the preferred pH range of the aqueous phase of the composition is pH 4.5 to 6.5, particularly preferably pH 5 to 6.

The compositions here are usually compositions which can be applied topically, for example cosmetic or dermatological formulations or medical products. In this case, the compositions comprise a cosmetically or dermatologically suitable vehicle and, depending on the desired property profile, optionally further suitable ingredients. In the case of pharmaceutical compositions, the compositions comprise a pharmaceutically tolerated excipient and optionally further pharmaceutical active compounds. In the case of food supplements, a vehicle which is suitable for this purpose should be selected.

If the compositions are perfumes, it is preferred in a variant of the invention for no further assistants to be present besides the fragrances or perfume oils and the flavonoids and typical carrier substances, such as water, solvents, such as alcohols, oils and optionally emulsifiers. In the case of odour-active perfume components, creatinine can be employed for controlled release of these components.

For the purposes of the present invention, the term preparation or formulation is also used synonymously alongside the term composition.

All compounds or components which can be used in the compositions are either known and commercially available or can be synthesised by known processes.

The present invention furthermore relates to a mixture, in particular a solid mixture, which comprises at least one α-amino acid derivative, preferably selected from 2-pyrrolidone-5-carboxylic acid, creatinine, creatine, ectoine and hydroxyectoine, and at least one sparingly soluble substance, preferably selected from chromones, chromanones, flavonoids and organic acids, in particular aromatic monosulfonic acids. This mixture is, in particular, suitable for the preparation of a cosmetic, pharmaceutical composition, a medical product or a food preparation.

In a preferred embodiment of the mixture according to the invention, the at least one α-amino acid derivative and the at least one sparingly soluble substance are present in a percent by weight ratio of 10:1 to 1.1:1, preferably 5:1 to 1.5:1, very particularly preferably 3.5:1 to 2:1.

In a further preferred embodiment, the mixture according to the invention comprises 90% by weight to 11% by weight of at least one α-amino acid derivative, as defined above, and 45% by weight to 10% by weight of at least one sparingly soluble substance, as defined above. Besides the two principal components, as defined above, the mixture may additionally comprise further substances, such as, for example, release agents. Release agents which can be employed are, for example, silicic acid (Aerosils), talc, zinc oxide or starch.

The sparingly soluble substance in the mixtures according to the invention is very particularly preferably an aromatic monosulfonic acid, preferably selected from the group of 2-arylbenzimidazole-5-sulfonic acids of the formula IV, as described above, 2-hydroxy-4-methoxybenzophenone-5-sulfonic acid or derivatives of 3-benzylidenecamphor. 2-Phenylbenzimidazole-5-sulfonic acid and sorbic acid or 2-phenylbenzimidazole-5-sulfonic acid or sorbic acid are particularly preferably selected as sparingly soluble substance in the mixture according to the invention. Creatinine is particularly preferably employed as α-amino acid derivative in the mixtures according to the invention.

Further preferred combinations of embodiments are disclosed in the claims.

The mixtures according to the invention can be prepared with the aid of techniques which are well known to the person skilled in the art. For example, the α-amino acid derivative is dissolved in a suitable solvent, preferably in water or an aqueous solution, the sparingly soluble substance is introduced, and the solvent is removed again using a suitable technique. For example, distillation, freeze drying or spray drying is suitable. Spray drying is particularly suitable.

The invention therefore furthermore also relates to a process for the preparation of a mixture, as described above, characterised in that an α-amino acid derivative is dissolved in a suitable solvent, the sparingly soluble substance and optionally a release agent are introduced, and the solvent is removed.

A preferred process for the preparation of mixtures comprising creatinine as α-amino acid derivative is characterised in that firstly creatine is dissolved in water at temperatures of 40° C. to 50° C., the sparingly soluble substance and optionally a release agent are subsequently introduced at temperatures of 40° C. to 50° C., and the solution is subjected to spray drying. The spray drying is carried out, for example, at a feed air temperature of 160° C. to 240° C. and a discharge air temperature of 80° C. to 120° C.

The compositions or mixtures may include or comprise, essentially consist of or consist of the said requisite or optional constituents.

In the compositions and mixtures described which, in accordance with the invention, comprise at least one derivative of an α-amino acid and at least one sparingly soluble substance, it is furthermore also possible for pigments to be present, where the layer structure of the pigments is not limited.

The coloured pigment should preferably be skin-coloured or brownish on use of 0.5% by weight to 5% by weight. The choice of a corresponding pigment is familiar to the person skilled in the art.

Advantageous coloured pigments are, for example, titanium dioxide, mica, iron oxides (for example $Fe_2O_3$, $Fe_3O_4$, FeO(OH)) and/or tin oxide. Advantageous dyes are, for example, carmine, Berlin Blue, Chromium Oxide Green, Ultramarine Blue and/or Manganese Violet.

It is particularly advantageous to select the dyes and/or coloured pigments from the following list. The Colour Index numbers (CINs) are taken from the Rowe. Colour Index, 3rd Edition, Society of Dyers and Colourists, Bradford, England, 1971.

| Chemical or other name | CIN | Colour |
| --- | --- | --- |
| Pigment Green | 10006 | Green |
| Acid Green 1 | 10020 | Green |
| 2,4-Dinitrohydroxynaphthalene-7-sulfonic acid | 10316 | Yellow |
| Pigment Yellow 1 | 11680 | Yellow |
| Pigment Yellow 3 | 11710 | Yellow |
| Pigment Orange 1 | 11725 | Orange |
| 2,4-dihydroxyazobenzene | 11920 | Orange |
| Solvent Red 3 | 12010 | Red |
| 1-(2'-chloro-4'-nitro-1'-phenylazo)-2-hydroxynaphthalene | 12085 | Red |
| Pigment Red 3 | 12120 | Red |
| Ceres Red; Sudan Red; Fat Red G | 12150 | Red |
| Pigment Red 112 | 12370 | Red |
| Pigment Red 7 | 12420 | Red |
| Pigment Brown 1 | 12480 | Brown |
| N-(5-Chloro-2,4-dimethoxyphenyl)-4-[[5-[(diethylamino)sulfonyl]-2-methoxyphenyl]azo]-3-hydroxynaphthalene-2-carboxamide | 12490 | Red |
| Disperse Yellow 16 | 12700 | Yellow |
| 1-(4-Sulfo-1-phenylazo)-4-aminobenzene-5-sulfonic acid | 13015 | Yellow |
| 2,4-dihydroxyazobenzene-4'-sulfonic acid | 14270 | Orange |
| 2-(2,4-dimethylphenylazo-5-sulfonyl)-1-hydroxynaphthalene-4-sulfonic acid | 14700 | Red |
| 2-(4-Sulfo-1-naphthylazo)-1-naphthol-4-sulfonic acid | 14720 | Red |
| 2-(6-Sulfo-2,4-xylylazo)-1-naphthol-5-sulfonic acid | 14815 | Red |
| 1-(4'-Sulfophenylazo)-2-hydroxynaphthalene | 15510 | Orange |
| 1-(2-Sulfonyl-4-chloro-5-carboxy-1-phenylazo)-2-hydroxynaphthalene | 15525 | Red |
| 1-(3-Methylphenylazo-4-sulfonyl)-2-hydroxynaphthalene | 15580 | Red |
| 1-(4',(8')-Sulfonylnaphthylazo)-2-hydroxynaphthalene | 15620 | Red |

-continued

| Chemical or other name | CIN | Colour |
|---|---|---|
| 2-Hydroxy-1,2'-azonaphthalene-1'-sulfonic acid | 15630 | Red |
| 3-Hydroxy-4-phenylazo-2-naphthylcarboxylic acid | 15800 | Red |
| 1-(2-Sulfo-4-methyl-1-phenylazo)-2-naphthylcarboxylic acid | 15850 | Red |
| 1-(2-Sulfo-4-methyl-5-chloro-1-phenylazo)-2-hydroxy-naphthalene-3-carboxylic acid | 15865 | Red |
| 1-(2-Sulfo-1-naphthylazo)-2-hydroxynaphtalene-3-carboxylic acid | 15880 | Red |
| 1-(3-Sulfo-1-phenylazo)-2-naphthol-6-sulfonic acid | 15980 | Orange |
| 1-(4-Sulfo-1-phenylazo)-2-naphthol-6-sulfonic acid | 15985 | Yellow |
| Allura Red | 16035 | Red |
| 1-(4-Sulfo-1-naphthylazo)-2-naphthol-3,6-disulfonic acid | 16185 | Red |
| Acid Orange 10 | 16230 | Orange |
| 1-(4-Sulfo-1-naphthylazo)-2-naphthol-6,8-disulfonic acid | 16255 | Red |
| 1-(4-Sulfo-1-naphthylazo)-2-naphthol-3,6,8-trisulfonic acid | 16290 | Red |
| 8-Amino-2-phenylazo-1-naphthol-3,6-disulfonic acid | 17200 | Red |
| Acid Red 1 | 18050 | Red |
| Acid Red 155 | 18130 | Red |
| Acid Yellow 121 | 18690 | Yellow |
| Acid Red 180 | 18736 | Red |
| Acid Yellow 11 | 18820 | Yellow |
| Acid Yellow 17 | 18965 | Yellow |
| 4-(4-Sulfo-1-phenylazo)-1-(4-sulfophenyl)-5-hydroxypyrazolone-3-carboxylic acid | 19140 | Yellow |
| Pigment Yellow 16 | 20040 | Yellow |
| 2,6-(4'-Sulfo-2'',4''-dimethyl)bisphenylazo-1,3-dihydroxybenzene | 20170 | Orange |
| Acid Black 1 | 20470 | Black |
| Pigment Yellow 13 | 21100 | Yellow |
| Pigment Yellow 83 | 21108 | Yellow |
| Solvent Yellow | 21230 | Yellow |
| Acid Red 163 | 24790 | Red |
| Acid Red 73 | 27290 | Red |
| 2-[4''-(4''-Sulfo-1''-phenylazo)-7'-sulfo-1'-naphthylazo]-1-hydroxy-7-aminonaphthalene-3,6-disulfonic acid | 27755 | Black |
| 4-[4''-Sulfo-1''-phenylazo)-7'-sulfo-1'-naphthylazo]-1-hydroxy-8-acetylaminonaphthalene-3,5-disulfonic acid | 28440 | Black |
| Direct Orange 34, 39, 44, 46, 60 | 40215 | Orange |
| Food Yellow | 40800 | Orange |
| trans-β-Apo-8'-carotene aldehyde ($C_{30}$) | 40820 | Orange |
| trans-Apo-8'-carotinic acid ($C_{30}$) ethyl ester | 40850 | Orange |
| Canthaxanthine | 40850 | Orange |
| Acid Blue 1 | 42045 | Blue |
| 2,4-Disulfo-5-hydroxy-4'-4''-bis(diethylamino)triphenylcarbinol | 42051 | Blue |
| 4-[(4-N-Ethyl-p-sulfobenzylamino)phenyl-(4-hydroxy-2-sulfo-phenyl)(methylene)-1-(N-ethyl-N-p-sulfobenzyl)-2,5-cyclo-hexadienimine] | 42053 | Green |
| Acid Blue 7 | 42080 | Blue |
| (N-Ethyl-p-sulfobenzylamino)phenyl-(2-sulfophenyl)methylene-(N-ethyl-N-p-sulfobenzyl)-$\Delta^{2,5}$-cyclohexadienimine | 42090 | Blue |
| Acid Green 9 | 42100 | Green |
| Diethyldisulfobenzyldi-4-amino-2-chlorodi-2-methylfuchson-immonium | 42170 | Green |
| Basic Violet 14 | 42510 | Violet |
| Basic Violet 2 | 42520 | Violet |
| 2'-Methyl-4'-(N-ethyl-N-m-sulfobenzyl)amino-4''-(N-diethyl)amino-2-methyl-N-ethyl-N-m-sulfobenzylfuchsonimmonium | 42735 | Blue |
| 4'-(N-Dimethyl)amino-4''-(N-phenyl)aminonaphtho-N-dimethyl-fuchsonimmonium | 44045 | Blue |
| 2-Hydroxy-3,6-disulfo-4,4'-bisdimethylaminonaphthofuchson-immonium | 44090 | Green |
| Acid Red 52 | 45100 | Red |
| 3-(2'-Methylphenylamino)-6-(2'-methyl-4'-sulfophenylamino)-9-(2''-carboxyphenyl)xanthenium salt | 45190 | Violet |
| Acid Red 50 | 45220 | Red |
| Phenyl-2-oxyfluorone-2-carboxylic acid | 45350 | Yellow |
| 4,5-Dibromofluorescein | 45370 | Orange |
| 2,4,5,7-Tetrabromofluorescein | 45380 | Red |
| Solvent Dye | 45396 | Orange |
| Acid Red 98 | 45405 | Red |
| 3',4',5',6'-Tetrachloro-2,4,5,7-tetrabromofluorescein | 45410 | Red |
| 4,5-Diiodofluorescein | 45425 | Red |
| 2,4,5,7-Tetraiodofluorescein | 45430 | Red |
| Quinophthalone | 47000 | Yellow |
| Quinophthalonedisulfonic acid | 47005 | Yellow |
| Acid Violet 50 | 50325 | Violet |
| Acid Black 2 | 50420 | Black |
| Pigment Violet 23 | 51319 | Violet |
| 1,2-Dioxyanthraquinone, calcium-aluminium complex | 58000 | Red |
| 3-Oxypyrene-5,8,10-sulfonic acid | 59040 | Green |

-continued

| Chemical or other name | CIN | Colour |
| --- | --- | --- |
| 1-Hydroxy-4-N-phenylaminoanthraquinone | 60724 | Violet |
| 1-Hydroxy-4-(4'-methylphenylamino)anthraquinone | 60725 | Violet |
| Acid Violet 23 | 60730 | Violet |
| 1,4-Di(4'-methylphenylamino)anthraquinone | 61565 | Green |
| 1,4-Bis(o-sulfo-p-toluidino)anthraquinone | 61570 | Green |
| Acid Blue 80 | 61585 | Blue |
| Acid Blue 62 | 62045 | Blue |
| N,N'-Dihydro-1,2,1',2'-anthraquinonazine | 69800 | Blue |
| Vat Blue 6; Pigment Blue 64 | 69825 | Blue |
| Vat Orange 7 | 71105 | Orange |
| Indigo | 73000 | Blue |
| Indigodisulfonic acid | 73015 | Blue |
| 4,4'-Dimethyl-6,6'-dichlorothioindigo | 73360 | Red |
| 5,5'-Dichloro-7,7'-dimethylthioindigo | 73385 | Violet |
| Quinacridone Violet 19 | 73900 | Violet |
| Pigment Red 122 | 73915 | Red |
| Pigment Blue 16 | 74100 | Blue |
| Phthalocyanine | 74160 | Blue |
| Direct Blue 86 | 74180 | Blue |
| Chlorinated phthalocyanine | 74260 | Green |
| Natural Yellow 6, 19; Natural Red 1 | 75100 | Yellow |
| Bixin, Nor-Bixin | 75120 | Orange |
| Lycopene | 75125 | Yellow |
| trans-alpha-, -beta- or -gamma-Carotene | 75130 | Orange |
| Keto and/or hydroxyl derivatives of carotene | 75135 | Yellow |
| Guanine or pearlescent agent | 75170 | White |
| 1,7-Bis(4-hydroxy-3-methoxyphenyl)-1,6-heptadiene-3,5-dione | 75300 | Yellow |
| Complex salt (Na, Al, Ca) of carminic acid | 75470 | Red |
| Chlorophyll a and b; copper compounds of chlorophylls and chlorophyllines | 75810 | Green |
| Aluminium | 77000 | White |
| Aluminium hydroxide | 77002 | White |
| Water-containing aluminium silicates | 77004 | White |
| Ultramarine | 77007 | Blue |
| Pigment Red 101 and 102 | 77015 | Red |
| Barium sulfate | 77120 | White |
| Bismuth oxychloride and mixtures thereof with mica | 77163 | White |
| Calcium carbonate | 77220 | White |
| Calcium sulfate | 77231 | White |
| Carbon | 77266 | Black |
| Pigment Black 9 | 77267 | Black |
| Carbo medicinalis vegetabilis | 77268:1 | Black |
| Chromium oxide | 77288 | Green |
| Chromium oxide, water-containing | 77278 | Green |
| Pigment Blue 28, Pigment Green 14 | 77346 | Green |
| Pigment Metal 2 | 77400 | Brown |
| Gold | 77480 | Brown |
| Iron oxides and hydroxides | 77489 | Orange |
| Iron oxide | 77491 | Red |
| Iron oxide hydrate | 77492 | Yellow |
| Iron oxide | 77499 | Black |
| Mixtures of iron(II) and iron(III) hexacyanoferrate | 77510 | Blue |
| Pigment White 18 | 77713 | White |
| Manganese ammonium diphosphate | 77742 | Violet |
| Manganese phosphate; $Mn_3(PO_4)_2 \cdot 7\ H_2O$ | 77745 | Red |
| Silver | 77820 | White |
| Titanium dioxide and mixtures thereof with mica | 77891 | White |
| Zinc oxide | 77947 | White |
| 6,7-Dimethyl-9-(1'-D-ribityl)isoalloxazine, lactoflavin | | Yellow |
| Sugar dye | | Brown |
| Capsanthin, capsorubin | | Orange |
| Betanin | | Red |
| Benzopyrylium salts, anthocyans | | Red |
| Aluminium, zinc, magnesium and calcium stearate | | White |
| Bromothymol Blue | | Blue |

Particular preference is given to the types of pearlescent pigment listed below:

1. Natural pearlescent pigments, such as, for example,
   "pearl essence" (guanine/hypoxanthine mixed crystals from fish scales) and
   "mother-of-pearl" (ground mussel shells)

2. Monocrystalline pearlescent pigments, such as, for example, bismuth oxychloride (BiOCl)

3. Layered substrate pigments: for example mica/metal oxide

The basis for pearlescent pigments is formed by, for example, pulverulent pigments or castor oil dispersions of bismuth oxychloride and/or titanium dioxide as well as bismuth oxychloride and/or titanium dioxide on mica. The lustre pigment listed under CIN 77163, for example, is particularly advantageous.

Also advantageous are, for example, the following pearlescent pigment types based on mica/metal oxide:

| Group | Coating/layer thickness | Colour |
|---|---|---|
| Silver-white pearlescent pigments | $TiO_2$: 40-60 nm | Silver |
| Interference pigments | $TiO_2$: 60-80 nm | Yellow |
| | $TiO_2$: 80-100 nm | Red |
| | $TiO_2$: 100-140 nm | Blue |
| | $TiO_2$: 120-160 nm | Green |
| Coloured lustre pigments | $Fe_2O_3$ | Bronze |
| | $Fe_2O_3$ | Copper |
| | $Fe_2O_3$ | Red |
| | $Fe_2O_3$ | Red-violet |
| | $Fe_2O_3$ | Red-green |
| | $Fe_2O_3$ | Black |
| Combination pigments | $TiO_2/Fe_2O_3$ | Gold shades |
| | $TiO_2/Cr_2O_3$ | Green |
| | $TiO_2$/Berlin Blue | Dark blue |

Particular preference is given to, for example, the pearlescent pigments available from Merck under the trade names Timiron®, Colorona®, Dichrona®, Xirona® or Ronastar®.

The list of the said pearlescent pigments is of course not intended to be limiting. Pearlescent pigments which are advantageous for the purposes of the present invention can be obtained by numerous routes known per se. For example, other substrates apart from mica can also be coated with further metal oxides, such as, for example, silica and the like. For example, $TiO_2$- and $Fe_2O_3$-coated $SiO_2$ particles ("Ronasphere" grades), which are marketed by Merck and are particularly suitable for the optical reduction of fine wrinkles, are advantageous.

It may additionally be advantageous to completely omit a substrate such as mica. Particular preference is given to pearlescent pigments prepared using $SiO_2$. Such pigments, which may additionally also have goniochromatic effects, are available, for example, from BASF under the trade name Sicopearl Fantastico.

It may also be advantageous to employ Engelhard/Mearl pigments based on calcium sodium borosilicate coated with titanium dioxide. These are available under the name Reflecks®. Due to their particle size of 40-80 μm, they have a glitter effect in addition to the colour.

Also particularly advantageous are effect pigments available from Flora Tech under the trade name Metasomes® Standard/Glitter in various colours (yellow, red, green, blue). The glitter particles here are in the form of mixtures with various assistants and dyes (such as, for example, the dyes with the colour index (CI) numbers 19140, 77007, 77289, 77491).

The composition or mixture according to the invention may, in addition, preferably also comprise further active substances, such as, for example, repellents, in particular insect repellents, UV filters, aryl oximes and parabens.

Most repellent active compounds belong to the substance classes of the amides, alcohols, esters and ethers. Repellents here should usually satisfy the following conditions: they must not evaporate too quickly and must not penetrate into the skin. They must not have a primary irritating or sensitising action on the skin and in addition should be non-toxic. Their efficacy must also be retained when exposed to skin moisture and/or UV radiation.

Preferred repellents are selected from N,N-diethyl-3-methylbenzamide, ethyl 3-(acetylbutylamino)propionate, dimethyl phthalate, butopyronoxyl, 2,3,4,5-bis(2-butylene)tetrahydro-2-furaldehyde, N,N-diethylcaprylamide, N,N-diethylbenzamide, o-chloro-N,N-diethylbenzamide, N-(2-ethylhexyl)-8,9,10-trinorborn-5-ene-2,3-dicarboximide, dimethyl carbate, di-n-propyl isocinchomeronate, (R)-p-mentha-1,8-diol, 2-ethylhexane-1,3-diol, N-octylbicyclohepetenedicarboximide, piperonyl butoxide, 1-(2-methylpropyloxycarbonyl)-2-(hydroxyethyl)piperidine (Bayrepel®; Bayer) or mixtures thereof, where they are particularly preferably selected from N,N-diethyl-3-methylbenzamide, ethyl 3-(acetylbutylamino)propionate, 1-(2-methylpropyloxycarbonyl)-2-(hydroxyethyl)piperidine or mixtures thereof.

Parabens are 4-hydroxybenzoic acid esters which are used in free form or as sodium salts for the preservation of compositions in the area of foods, cosmetics and medicaments. The action of the esters is directly proportional to the chain length of the alkyl radical, but conversely the solubility decreases with increasing chain length. As non-dissociating compounds, the esters are substantially pH-independent and act in a pH range of 3.0-8.0. The antimicrobial action mechanism is based on damage of the microbe membranes by the surface activity of the PHB esters and on protein denaturing. In addition, interactions occur with coenzymes. The action is directed against fungi, yeasts and bacteria. The most important parabens as preservatives are methyl 4-hydroxybenzoate, ethyl 4-hydroxybenzoate, propyl 4-hydroxybenzoate and butyl 4-hydroxybenzoate.

Of the aryl oximes, preference is given to the use of 2-hydroxy-5-methyllaurophenone oxime, which is also known as HMLO, LPO or F5. Its suitability for use in cosmetic compositions is disclosed, for example, in DE 41 16 123. Compositions which comprise 2-hydroxy-5-methyllaurophenone oxime are accordingly suitable for the treatment of skin diseases which are accompanied by inflammation. It is known that compositions of this type can be used, for example, for the therapy of psoriasis, various forms of eczema, irritative and toxic dermatitis, UV dermatitis and other allergic and/or inflammatory diseases of the skin and skin appendages. Compositions according to the invention which, in addition to the said compound(s), additionally comprise an aryl oxime, preferably 2-hydroxy-5-methyllaurophenone oxime, exhibit surprising anti-inflammatory suitability. The compositions here preferably comprise 0.01 to 10% by weight of the aryl oxime, it being particularly preferred for the composition to comprise 0.05 to 5% by weight of aryl oxime.

The protective action of compositions against oxidative stress or against the action of free radicals can be improved if the compositions comprise one or more antioxidants, where the person skilled in the art is presented with absolutely no difficulties in selecting antioxidants which act suitably quickly or in a delayed manner.

In a preferred embodiment, the composition is therefore a composition for the protection of body cells against oxidative stress, in particular for reducing skin ageing, characterised in that it comprises one or more antioxidants besides the other ingredients.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to μmol/kg), and also (metal) chelating agents (for example α-hydroxy-fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Suitable antioxidants are also compounds of the general formula A or B

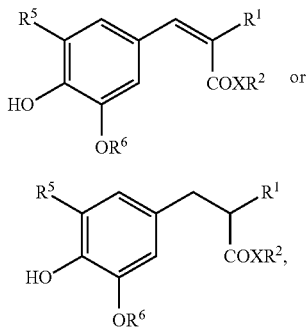

in which
$R^1$ can be selected from the group —$C(O)CH_3$, —$CO_2R^3$, —$C(O)NH_2$ and —$C(O)N(R^4)_2$,
X denotes O or NH,
$R^2$ denotes linear or branched alkyl having 1 to 30 C atoms,
$R^3$ denotes linear or branched alkyl having 1 to 20 C atoms,
$R^4$ in each case, independently of one another, denotes H or linear or branched alkyl having 1 to 8 C atoms,
$R^5$ denotes H or linear or branched alkyl having 1 to 8 C atoms or linear or branched alkoxy having 1 to 8 C atoms, and
$R^6$ denotes linear or branched alkyl having 1 to 8 C atoms, preferably derivatives of 2-(4-hydroxy-3,5-dimethoxybenzylidene)malonic acid and/or 2-(4-hydroxy-3,5-dimethoxybenzyl)malonic acid, particularly preferably bis (2-ethylhexyl) 2-(4-hydroxy-3,5-dimethoxybenzylidene) malonate (for example Oxynex® ST Liquid) and/or bis(2-ethylhexyl) 2-(4-hydroxy-3,5-dimethoxybenzyl)malonate (for example RonaCare® AP).

Mixtures of antioxidants are likewise suitable for use in the cosmetic compositions according to the invention. Known and commercial mixtures are, for example, mixtures comprising, as active ingredients, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Anti-oxidants of this type are usually employed in such compositions with the compounds according to the invention in percent by weight ratios in the range from 1000:1 to 1:1000, preferably in percent by weight ratios of 100:1 to 1:100.

Suitable antioxidants are furthermore compounds of the formula (C)

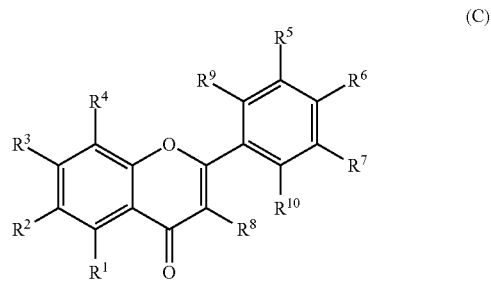

Where
$R^1$ to $R^{10}$ may be identical or different and are selected from
H,
$OR^{11}$,
straight-chain or branched $C_1$- to $C_{20}$-alkyl groups,
straight-chain or branched $C_3$- to $C_{20}$-alkenyl groups,
straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and/or
$C_3$- to $C_{10}$-cycloalkyl groups and/or $C_3$- to $C_{12}$-cycloalkenyl groups, where the rings may each also be bridged by —$(CH_2)_n$— groups, where n=1 to 3,
where all $OR^{11}$, independently of one another, stand for OH,
straight-chain or branched $C_1$- to $C_{20}$-alkoxy groups,
straight-chain or branched $C_3$- to $C_{20}$-alkenyloxy groups,
straight-chain or branched $C_1$- to $C_{20}$-hydroxyalkoxy groups, where the hydroxyl group(s) may be bonded to a primary or secondary carbon atom of the chain and furthermore the alkyl chain may also be interrupted by oxygen, and/or
$C_3$- to $C_{10}$-cycloalkoxy groups and/or $C_3$- to $C_{12}$-cycloalkenyloxy groups, where the rings may each also be bridged by —$(CH_2)_n$— groups, where n=1 to 3, and/or
mono- and/or oligoglycosyl radicals,
with the proviso that at least 4 radicals from $R^1$ to $R^7$ stand for OH and that at least 2 pairs of adjacent —OH groups are present in the molecule,
or $R^2$, $R^5$ and $R^6$ stand for OH and the radicals $R^1$, $R^3$, $R^4$ and $R^{7-10}$ stand for H,
as described in German patent application DE-A-102 44 282.

The compositions or mixtures to be employed may comprise vitamins as further ingredients. Preference is given to vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active compound), thiamine (vitamin $B_1$), nicotinic acid (niacin), pyridoxine, pyridoxal, pyridoxamine (vitamin $B_6$), pantothenic acid, biotin, folic acid and cobalamine (vitamin $B_{12}$), particularly preferably vitamin A palmitate, vitamin C and derivatives thereof, DL-α-tocopherol, tocopherol E acetate, nicotinic acid, pantothenic acid and biotin. In cosmetic applications, vitamins are, usually added with the flavonoid-containing premixes or compositions in ranges from 0.01 to 5.0% by weight, based on the total weight. Nutrition-physiological applications depend on the respective recommended vitamin need.

Preferred compositions may also serve for sun protection. Compositions or mixtures according to the invention may therefore also comprise UV filters besides α-amino acid derivatives and the sparingly soluble substances and any other ingredients.

In principle, all UV filters are suitable for combination with the α-amino acid derivatives to be employed in accordance with the invention. Particular preference is given to UV filters whose physiological acceptability has already been demonstrated. Both for UVA and UVB filters, there are many proven substances which are known from the specialist literature, for example benzylidenecamphor derivatives, such as 3-(4'-methylbenzylidene)-dl-camphor (for example Eusolex® 6300), 3-benzylidenecamphor (for example Mexoryl® SD), polymers of N-{(2 and 4)-[(2-oxoborn-3-ylidene)methyl]benzyl}acrylamide (for example Mexoryl® SW) or N,N,N-trimethyl-4-(2-oxoborn-3-ylidenemethyl)anilinium methylsulfate (for example Mexoryl® SK))

benzoyl- or dibenzoylmethanes, such as 1-(4-tert-butylphenyl)-3-(4-methoxy-phenyl)propane-1,3-dione (for example Eusolex® 9020) or 4-isopropyldibenzoylmethane (for example Eusolex® 8020), benzophenones, such as 2-hydroxy-4-methoxybenzophenone (for example Eusolex® 4360) or the sodium salt of 2-hydroxy-4-methoxybenzophenone-5-sulfonic acid, methoxycinnamic acid esters, such as octyl methoxycinnamate (for example Eusolex® 2292), isopentyl 4-methoxycinnamate, for example as a mixture of the isomers (for example Neo Heliopan® E 1000), salicylate derivatives, such as 2-ethylhexyl salicylate (for example Eusolex® OS), 4-isopropylbenzyl salicylate (for example Megasol®) or 3,3,5-trimethylcyclohexyl salicylate (for example Eusolex® HMS), potassium, sodium and triethanolamine salts of phenylbenzimidazolesulfonic acids, such as 2-phenylbenzimidazole-5-sulfonic acid, 2,2-(1,4-phenylene)bis-benzimidazole-4,6-disulfonic acid and salts thereof (for example Neoheliopan® AP), and further substances, such as 2-ethylhexyl 2-cyano-3,3-diphenylacrylate (for example Eusolex® OCR), 3,3'-(1,4-phenylenedimethylene)bis(7,7-dimethyl-2-oxobicyclo[2.2.1]hept-1-yl-methanesulfonic acid and salts thereof (for example Mexoryl® SX), 2,4,6-trianilino-(p-carbo-2'-ethylhexyl-1'-oxy)-1,3,5-triazine (for example Uvinul® T 150), and hexyl 2-(4-diethylamino-2-hydroxybenzoyl)benzoate (for example Uvinul® UVA Plus, BASF).

The compounds mentioned in the list should only be regarded as examples. It is of course also possible to use other UV filters.

Further suitable organic UV filters are, for example, 2-(2H-benzotriazol-2-yl)-4-methyl-6-(2-methyl-3-(1,3,3,3-tetramethyl-1-(trimethylsilyloxy)disiloxanyl)propyl)phenol (for example Silatrizole®, drometrizoles, trisiloxanes, Mexoryl® XL), 2-ethylhexyl 4,4'-[(6-[4-((1,1-dimethylethyl)aminocarbonyl)phenylamino]-1,3,5-triazine-2,4-diyl)diimino]bis(benzoate) (for example Uvasorb® HEB), α-(trimethylsilyl)-ω-[trimethylsilyl)oxy]poly[oxy(dimethyl) [and about 6% of methyl[2-[p-[2,2-bis(ethoxycarbonyl)vinyl]phenoxy]-1-methyleneethyl] and about 1.5% of methyl[3-[p-[2,2-bis(ethoxycarbonyl)vinyl)phenoxy)propenyl) and 0.1 to 0.4% of (methylhydrogen)silylene]] (n≈60) (CAS No. 207 574-74-1), 2,2'-methylenebis(6-(2H-benzotriazol-2-yl)-4-(1,1,3,3-tetramethylbutyl)phenol) (CAS No. 103 597-45-1), 2,2'-(1,4-phenylene)bis(1H-benzimidazole-4,6-disulfonic acid, monosodium salt) (CAS No. 180 898-37-7), and 2,4-bis{[4-(2-ethylhexyloxy)-2-hydroxy]phenyl}-6-(4-methoxyphenyl)-1,3,5-triazine (CAS No. 103 597-45-, 187 393-00-6).

Further suitable UV filters are also methoxyflavones corresponding to German patent application DE-A-10232595.

Organic UV filters are generally incorporated into formulations in an amount of 0.5 to 20 percent by weight, preferably 1-15% by weight.

In order to ensure optimised UV protection, it is furthermore preferred for compositions having light-protection properties also to comprise inorganic UV filters. Conceivable inorganic UV filters are those from the group of the titanium dioxides, such as, for example, coated titanium dioxide (for example Eusolex® T-2000, Eusolex® T-AQUA, Eusolex® T-AVO), zinc oxides (for example Sachtotec®), iron oxides or also cerium oxides. These inorganic UV filters are generally incorporated into cosmetic compositions in an amount of 0.5 to 20 percent by weight, preferably 2-10% by weight.

Preferred compounds having UV-filtering properties are 3-(4'-methylbenzylidene)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxy-cinnamate, 3,3,5-trimethylcyclohexyl salicylate, 2-ethylhexyl 4-(dimethylamino)-benzoate, 2-ethylhexyl 2-cyano-3,3-diphenylacrylate, 2-phenylbenzimidazole-5-sulfonic acid and potassium, sodium and triethanolamine salts thereof.

The protective action against the harmful effects of UV radiation can be optimised by combining one or more of the said compounds having a UV-filter action.

All the said UV filters can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin are repeatedly discussed in the literature. The encapsulation of the corresponding substances which is proposed here suppresses this effect.

In general, encapsulation of individual UV filters or other ingredients enables formulation problems caused by the interaction of individual composition constituents with one another, such as crystallisation processes, precipitation and agglomerate formation, to be avoided since the interaction is suppressed.

It is therefore preferred for one or more of the above-mentioned UV filters to be in encapsulated form. It is advantageous here for the capsules to be so small that they cannot be viewed with the naked eye. In order to achieve the above-mentioned effects, it is furthermore necessary for the capsules to be sufficiently stable and the encapsulated active compound (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules particularly preferably to be employed have walls which can be obtained by a sol-gel process, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules in compositions to be employed in accordance with the invention are preferably present in amounts which ensure that the encapsulated UV filters are present in the composition in the percent by weight ratios indicated above.

The compositions to be employed in accordance with the invention may, in addition, comprise further conventional skin-protecting or skin-care active compounds. These can in principle be all active compounds known to the person skilled in the art.

Particularly preferred active compounds, in particular for skin-care compositions, are, for example, also so-called compatible solutes. These are substances which are involved in the osmoregulation of plants or microorganisms and can be isolated from these organisms. The generic term compatible solutes here also encompasses the osmolytes described in German patent application DE-A-10133202. Suitable osmolytes are, for example, the polyols, methylamine compounds and amino acids and the respective precursors thereof. For the purposes of German patent application DE-A-10133202, osmolytes are taken to mean, in particular, substances from the group of the polyols, such as, for example, myoinositol, mannitol or sorbitol, and/or one or more of the osmolytically active substances mentioned below: taurine, choline, betaine, phosphorylcholine, glycerophosphorylcholines, glutamine, glycine, α-alanine, glutamate, aspartate, proline, and taurine. Precursors of these substances are, for example, glucose, glucose polymers, phosphatidylcholine, phosphatidylinositol, inorganic phosphates; proteins, peptides and polyamino acids. Precursors are, for example, compounds which are converted into osmolytes by metabolic steps.

Compatible solutes, as described above, can be employed in the compositions or mixtures according to the invention, preferably in amounts of up to 15% by weight.

It is particularly preferred here for the compatible solutes to be selected from dimyo-inositol phosphate (DIP), cyclic 2,3-diphosphoglycerate (cDPG), 1,1-diglycerol phosphate (DGP), β-mannosyl glycerate (firoin), β-mannosylglyceramide (firoin-A) and/or dimannosyl diinositol phosphate (DMIP) or mixtures thereof.

The compositions or mixtures according to the invention may furthermore comprise at least one self-tanning agent as further ingredient.

Advantageous self-tanning agents which can be employed are, inter alia:

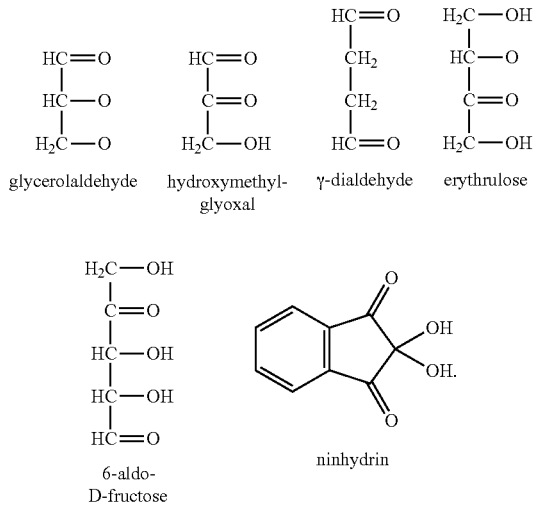

Mention should furthermore be made of 5-hydroxy-1,4-naphthoquinone (juglone), which is extracted from the shells of fresh walnuts

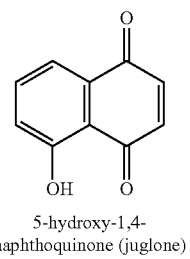

5-hydroxy-1,4-
naphthoquinone (juglone)

and 2-hydroxy-1,4-naphthoquinone (lawsone), which occurs in henna leaves,

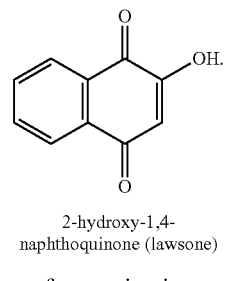

2-hydroxy-1,4-
naphthoquinone (lawsone)

Very particular preference is given to 1,3-dihydroxyacetone (DHA), a trifunctional sugar which occurs in the human body, and derivatives thereof

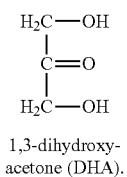

1,3-dihydroxy-
acetone (DHA).

Particular preference is likewise given to a mixture comprising dihydroxyacetone and creatinine and PBSA in a creatinine/PBSA mixing ratio of 3:1. The use according to the invention of creatinine together with PBSA in the stated mixing ratios, as described above, enables for the first time the preparation of a composition comprising DHA having an acidic pH, preferably in pH ranges as described above, and PBSA.

The α-amino acid derivatives and the sparingly soluble substances as well as any other active compounds or the mixtures according to the invention can be incorporated into compositions in the usual manner, for example by mixing.

Suitable compositions are those for external use, for example in the form of a cream, lotion, gel or as a solution which can be sprayed onto the skin. Suitable for internal use are administration forms such as capsules, coated tablets, powders, tablet solutions or solutions.

Examples which may be mentioned of application forms of the compositions to be employed are: solutions, suspensions, emulsions, PIT emulsions, pastes, ointments, gels, creams, lotions, powders, soaps, surfactant-containing cleansing preparations, oils, aerosols and sprays. Preferred application forms are also shampoos, tanning lotions and shower products, which are also known from commercial self-tanning studios as spray tans or airbrush tans.

Preferred assistants originate from the group of preservatives, stabilisers, solubilisers, colorants, odour improvers.

Ointments, pastes, creams and gels may comprise the customary vehicles, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary readily volatile, liquefied propellants, for example chlorofluorocarbons, propane/butane or dimethyl ether. Compressed air can also advantageously be used.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, powder make-up, emulsion make-up and wax make-up, and sunscreen, pre-sun and after-sun compositions.

The preferred composition forms also include, in particular, emulsions.

Emulsions are advantageous and comprise, for example, the said fats, oils, waxes and other fatty substances, as well as water and an emulsifier, as usually used for a composition of this type.

The lipid phase may advantageously be selected from the following group of substances:
mineral oils, mineral waxes;
oils, such as triglycerides of capric or caprylic acid, furthermore natural oils, such as, for example, castor oil;
fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of esters of saturated and/or unsaturated, branched and/or unbranched alkane-carboxylic acids having a chain length of 3 to 30 C atoms and saturated and/or unsaturated, branched and/or unbranched alcohols having a chain length of 3 to 30 C atoms, or from the group of esters of aromatic carboxylic acids and saturated and/or unsaturated, branched and/or unbranched alcohols having a chain length of 3 to 30 C atoms. Ester oils of this type can then advantageously be selected from the group of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group of branched and unbranched hydrocarbons and hydrocarbon waxes, silicone oils, dialkyl ethers, or the group of saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18 C atoms. The fatty acid triglycerides may advantageously be selected, for example, from the group of synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The aqueous phase of the compositions to be employed optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group of silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination.

In particular, mixtures of the above-mentioned solvents are used. In the case of alcoholic solvents, water may be a further constituent.

Emulsions are advantageous and comprise, for example, the said fats, oils, waxes and other fatty substances, as well as water and an emulsifier, as usually used for a formulation of this type.

In a preferred embodiment, the compositions to be employed comprise hydrophilic surfactants. The hydrophilic surfactants are preferably selected from the group of the alkylglucosides, acyl lactylates, betaines and coconut amphoacetates.

It is likewise advantageous to employ natural or synthetic raw materials and assistants or mixtures which are distinguished by an effective content of the active compounds used in accordance with the invention, for example Plantaren® 1200 (Henkel KGaA), Oramix® NS 10 (Seppic).

The cosmetic and dermatological compositions may exist in various forms. Thus, they may be, for example, a solution, a water-free composition, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer ectoines in encapsulated form, for example in collagen matrices and other conventional encapsulation materials, for example as cellulose encapsulations, in gelatine, wax matrices or liposomally encapsulated. In particular, wax matrices, as described in DE-A-43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions.

The co-emulsifiers selected are advantageously, for example, O/W emulsifiers, principally from the group of substances having HLB values of 11-16, very particularly advantageously having HLB values of 14.5-15.5, so long as the O/W emulsifiers have saturated radicals R and R'. If the O/W emulsifiers have unsaturated radicals R and/or R' or if isoalkyl derivatives are present, the preferred HLB value of such emulsifiers may also be lower or higher.

It is advantageous to select the fatty alcohol ethoxylates from the group of ethoxylated stearyl alcohols, cetyl alcohols, cetylstearyl alcohols (cetearyl alcohols). Particular preference is given to the following: polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:
polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group of polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group of polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

The following can be employed as optional W/O emulsifiers, but ones which may nevertheless be advantageous in accordance with the invention:
fatty alcohols having 8 to 30 carbon atoms, monoglycerol esters of saturated and/or unsaturated, branched and/or unbranched alkanecarboxylic acids having a chain length of 8 to 24, in particular 12-18 C atoms, diglycerol esters of saturated and/or unsaturated, branched and/or unbranched alkanecarboxylic acids having a chain length of 8 to 24, in particular 12-18 C atoms, monoglycerol ethers of saturated and/or unsaturated, branched and/or unbranched alcohols having a chain length of 8 to 24, in particular 12-18 C atoms, diglycerol ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

Compositions which are preferred in accordance with the invention are also suitable for protecting human skin against ageing processes and against oxidative stress, i.e. against damage caused by free radicals, as are generated, for example, by sunlight, heat or other influences. In this connection, they are in the various administration forms usually used for this application. For example, they may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants that are usually used in this type of composition, such as, for example, thickeners, softeners, moisturisers, surface-active agents, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or a lower polyol or mixtures thereof. Particularly preferred monoalcohols or polyols include ethanol, i-propanol, propylene glycol, glycerol and sorbitol.

A preferred embodiment of the invention is an emulsion in the form of a protective cream or milk which comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycol, such as propylene glycol, and/or a polyol, such as glycerol, and oils, waxes and fatty acid esters, such as triglycerides of fatty acids.

The composition may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, use is generally made of the customary propellants, such as alkanes, fluoroalkanes and chlorofluoroalkanes, preferably alkanes.

The compositions to be employed can be prepared with the aid of techniques which are well known to the person skilled in the art.

A process for the preparation of a composition according to the invention, as described above, can be mixing of the at least one α-amino acid derivative with at least one sparingly soluble substance or a mixture according to the invention and a vehicle which is suitable for topical applications, for example a cosmetically, pharmaceutically or dermatologically suitable vehicle. The mixing can result in dissolution, emulsification or dispersion in the vehicle.

Even without further comments, it is assumed that a person skilled in the art will be able to utilise the above description in the broadest scope. The preferred embodiments and examples should therefore merely be regarded as descriptive disclosure which is absolutely not limiting in any way. The complete disclosure content of all applications and publications mentioned above and below is incorporated into this application by way of reference. The percent by weight ratios of the individual ingredients in the compositions of the examples expressly belong to the disclosure content of the description and can therefore be employed as features.

The examples of the subject-matter according to the invention that are given below serve merely for explanation and in no way restrict the present invention at all. In addition, the invention described can be carried out throughout the entire scope claimed. All compounds or components which can be used in the compositions are either known and commercially available or can be synthesised by known methods. The INCI names of the raw materials used are given (the INCI names are by definition given in English).

EXAMPLES

Increase in the Solubilities of Tiliroside and 5,7-dihydroxy-2-methyl-chromone

Firstly, 4% ectoine solutions are prepared in water and in a water/ethanol mixture (3:1). The active compound to be dissolved is subsequently incorporated into the two ectoine solutions in an amount of 1% and 1.5% respectively. The respective ectoine-free batches serve as comparison. The assessment of the increase in solubility due to ectoine is carried out visually (clear solution in combination with ectoine, cloudy solution in the absence of ectoine).

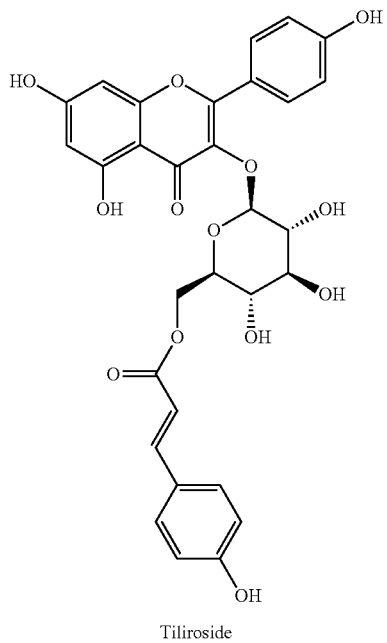

Tiliroside

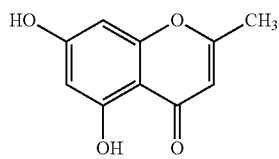

5,7-Dihydroxy-2-methylchromone

|  | Ethanol/water 3:1 | 4% of ectoine in ethanol/water 3:1 |
|---|---|---|
| Tiliroside, 1% | cloudy solution | clear solution |
| 5,7-Dihydroxy-2-methyl-chromone, 1.5% | cloudy solution | clear solution |

Increase in the Solubility of Phenylbenzimidazolesulfonic Acid (PBSA):

Firstly, 4% aqueous solutions of ectoine, creatinine and pyrrolidonecarboxylic acid are prepared. The active compound PBSA is subsequently dispersed in the solution in excess. The pH of the suspension is adjusted to 4.6. Undissolved active compound is filtered off after stirring for 1 hour. The dissolved active-compound fraction is determined by high-performance liquid chromatography. The experiment without solubiliser serves as comparison. In the case of dissolution of PBSA in aqueous creatinine solution, the solubility is additionally determined at pH 5.7, i.e. in this case the pH is not restored to 4.6.

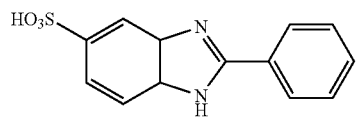

Phenylbenzimidazolesulfonic acid (PBSA)

Results:

| | |
|---|---|
| Solubility of PBSA in water (pH of the dispersion set to 4.6): | 0.34 g/l |
| Solubility of PBSA in water comprising 4% of ectoine (pH of the dispersion set to 4.6): | 0.60 g/l |
| Solubility of PBSA in water comprising 4% of creatinine (pH of the dispersion set to 4.6): | 0.94 g/l |
| Solubility of PBSA in water comprising 4% of creatinine (pH of the dispersion 5.7): | 8.50 g/l |
| Solubility of PBSA in water comprising 4% of pyrrolidonecarboxylic acid (pH of the dispersion set to 4.6): | 0.34 g/l |

Examples of cosmetic formulations comprising various mixtures M1, M2, M3, as described below:

| Illustrative formulations A to G for cosmetic emulsions | | | | | | | |
|---|---|---|---|---|---|---|---|
|  | A | B | C | D | E | F | G |
| Glyceryl stearate | 1 | 1 | 1 | 1 | 1 | 1 | 1 |
| Stearic acid | 3 | 3 | 3 | 3 | 3 | 3 | 3 |
| Behenyl alcohol | 2 | 2 | 2 | 2 | 2 | 2 | 2 |
| Cetyl alcohol | 2 | 2 | 2 | 2 | 2 | 2 | 2 |
| Hydrogenated coconut fatty glyceride | 1 | 1 | 1 | 1 | 1 | 1 | 1 |
| C12-15 Alkyl benzoate | 2 | 2 | 2 | 2 | 2 | 2 | 2 |
| Octyldodecanol | 2 | 2 | 2 | 2 | 2 | 2 | 2 |
| Octamethyltetrasiloxane (cyclomethicone) | 2 | 2 | 2 | 2 | 2 | 2 | 2 |
| Dimethylpolysiloxane (dimethicone) | 1 | 1 | 1 | 1 | 1 | 1 | 1 |
| Dicaprylyl carbonate | 4 | 4 | 4 | 4 | 2 | 2 | 2 |
| Butylmethoxydibenzoylmethane | 1 |  |  |  | 1 | 1 | 2 |
| Ethylhexyl methoxycinnamate | 2 |  | 2 |  | 4 | 4 | 6 |
| Titanium dioxide (Eusolex T-Avo) | 0.5 | 1 | 1 | 2 | 0.5 | 1 |  |
| Methylenebisbenzotriazolyltetramethyl-butylphenol (Tinosorb ® M) |  | 3 |  |  |  |  |  |
| Bisethylhexyloxyphenolmethoxyphenyl-triazine (Tinosorb ® S) |  |  | 1 | 2 |  |  |  |
| Bisethylhexyl hydroxydimethoxybenzyl-malonate (RonaCare ® AP) | 0.5 | 1.0 | 2.0 | 0.5 | 1.5 | 0.25 | 1.5 |
| Ubiquinone (Q10) | 0.05 |  | 0.05 |  | 0.05 |  | 0.05 |
| Panthenol |  | 0.5 |  | 0.5 | 0.5 | 0.5 |  |

Illustrative formulations A to G for cosmetic emulsions

|  | A | B | C | D | E | F | G |
|---|---|---|---|---|---|---|---|
| Mixture M1 | 2 | 4 | 8 |  |  |  |  |
| Mixture M2 |  |  |  | 1 | 2 |  |  |
| Mixture M3 |  |  |  |  |  | 1 | 2 |
| Sodium ascorbyl phosphate | 0.3 | 0.3 | 0.3 | 0.3 | 0.3 | 0.3 | 0.3 |
| Tocopheryl acetate | 0.5 | 0.5 | 0.5 | 0.5 | 0.5 | 0.5 | 0.5 |
| Iminodisuccinate | 0.2 | 0.2 | 0.2 | 0.2 | 0.2 | 0.2 | 0.2 |
| Phenoxyethanol | 0.3 | 0.3 | 0.3 | 0.3 | 0.3 | 0.3 | 0.3 |
| Alkyl p-hydroxybenzoate (paraben) | 0.6 | 0.6 | 0.6 | 0.6 | 0.6 | 0.6 | 0.6 |
| Ethanol, denatured | 3 | 3 | 3 | 3 | 3 | 3 | 3 |
| Carrageenan | 0.1 | 0.1 | 0.1 | 0.1 | 0.1 | 0.1 | 0.1 |
| Polyacrylic acid (Carbomer) | 0.1 | 0.2 | 0.3 | 0.05 | 0.1 | 0.05 | 0.1 |
| Glycerol | 7 | 5 | 3 | 5 | 5 | 5 | 5 |
| Perfume | 0.5 | 0.5 | 0.5 | 0.5 | 0.5 | 0.5 | 0.5 |
| NaOH/citric acid | q.s. for setting pH = 5.5 | | | | | | |
| Water | to 100 | to 100 | to 100 | to 100 | to 100 | to 100 | to 100 |

Depending on the intended action, the formulations indicated may optionally comprise a self-tanning substance (for example 0.5-10% of dihydroxyacetone and/or erythrulose) and/or a flavonoid (for example 025-3% of troxerutin, tiliroside) and/or an ascorbic acid derivative (for example 0.1-5% of ascorbic acid, ascorbyl palmitate and/or a substance in accordance with WO 2008017346).

Examples of mixtures M1, M2, M3, M4, M5:

Mixture M1:
Composition in Percent by Weight: 75% of Creatinine, 25% of PBSA
Preparation Process 1:
30 g of creatinine are dissolved in 500 ml of water with stirring at room temperature, 10 g of PBSA (Eusolex® 232) are subsequently introduced. The solvents are removed in vacuo (60 mbar) and a bath temperature of 50° C. The white solid mixture is dried for a further 48 h at 200 mbar and 40° C. in a drying cabinet and subsequently sieved (100 µm sieve).
Preparation Process 2:
30 g of creatinine are dissolved in 400 ml of water with stirring at room temperature, 10 g of PBSA (Eusolex® 232) are subsequently introduced. After spray drying, a white powder is obtained which dissolves in water and gives a pH of less than pH 6.
Preparation Process 3:
35 g of creatine are dissolved in 400 ml of water with stirring at room temperature, and the mixture is heated under reflux until complete conversion into creatinine has occurred. 10 g of PBSA (Eusolex® 232) are then introduced. After spray drying, a white powder is obtained which dissolves in water and gives a pH of less than pH 6.

Mixture M2:
Composition in Percent by Weight: 80% of Ectoine, 20% of Tiliroside
Preparation:
30 g of ectoine are added to 500 ml of ethanol/water mixture (3:1) with stirring at room temperature. 7.5 g of tiliroside are subsequently introduced. The solvents are removed in vacuo (60 mbar) and a bath temperature of 50° C. The yellow solid mixture is dried for a further 48 h at 200 mbar and 40° C. in a drying cabinet and passed through a 100 µm sieve. As an alternative drying method, the ethanol/water mixture can also be spray-dried.

Mixture M3:
Composition in Percent by Weight: 70% of Creatinine, 21% of Isoquercetin, 8.5% of Silicic Acid Preparation:
25 g of creatinine are added to 500 ml of ethanol/water mixture (3:1) with stirring at room temperature. 7.5 g of isoquercetin are subsequently introduced. The solvents are removed in vacuo (60 mbar) and a bath temperature of 50° C. 3 g of silicic acid are added to the yellow solid mixture, the mixture is dried for a further 48 h at 200 mbar and 40° C. in a drying cabinet and passed through a 100 µm sieve. As an alternative to the use of silicic acid (for example Aerosils, such as Aeroperl 300/30), starch, talc or zinc oxide can be used as alternative release agents.

Mixture M4:
Composition in Percent by Weight: 60% of Creatinine, 40% of Sorbic Acid
Preparation:
30 g of creatinine are dissolved in 400 ml of water with stirring at room temperature, 20 g of sorbic acid are subsequently introduced. After spray drying, a white powder is obtained which dissolves in water and gives a pH of less than pH 6.

Mixture M5:
2 parts by weight of mixture M1 are mixed homogeneously with 1 part by weight of dihydroxyacetone (DHA). This operation is preferably carried out under inertised conditions in order to prevent oxidation losses of DHA. Inertised conditions are, for example, the preparation of the mixture with exclusion of UV rays, in the presence of protective gases or also at low temperatures.

The invention claimed is:
1. A method for improving the solubility of a sparingly soluble substance which is an organic acid which comprises:
   (a) adding at least one α-amino acid derivative that is 2-pyrrolidone-5-carboxylic acid, creatinine, creatine, hydroxyectoine or a salt or hydrate thereof to a water- or aqueous-solutions, each comprising one or more sparingly soluble substances which are organic acids,
   (b) adding one or more sparingly soluble substances which are organic acids to a water- or aqueous-solutions, each comprising at least one α-amino acid derivative that is 2-pyrrolidone-5-carboxylic acid, creatinine, creatine, hydroxyectoine or a salt or hydrate thereof
   or
   (c) adding a mixture of one or more sparingly soluble substances which are organic acids and at least one α-amino acid derivative that is 2-pyrrolidone-5-car- boxylic acid, creatinine, creatine, hydroxyectoine or a salt or hydrate thereof, to water or to an aqueous solution.

2. The method according to claim 1, wherein the at least one α-amino acid derivative is 2-pyrrolidone-5-carboxylic acid.

3. The method according to claim 1, wherein the at least one α-amino acid derivative is added in an amount of 0.05 to 20% by weight.

4. The method according to claim 1, wherein the at least one α-amino acid derivative and the at least one sparingly soluble substance are used in a percent by weight ratio of 10:1 to 1.1:1.

5. The method according to claim 1, wherein the solubility of a substance whose solubility in water at a temperature between 20° C. and 25° C. is less than 1% by weight if the pH of the solution is less than pH 7 is improved.

6. The method according to claim 1, wherein the sparingly soluble substance is selected from 2-arylbenzimidazole-5-sulfonic acids, 2-hydroxy-4-methoxybenzophenone-5-sulfonic acid or sulfonic acid derivatives of 3-benzylidenecamphor.

7. The method according to claim 1, wherein the sparingly soluble substance is selected from benzoic acid, benzylic acid, formic acid, propionic acid, salicylic acid or sorbic acid.

8. A composition comprising at least one α-amino acid that is 2-pyrrolidone-5-carboxylic acid, creatinine, creatine, hydroxyectoine or a salt or hydrate thereof and at least one aromatic monosulfonic acid, where the proportion of the α-amino acid derivative in percent by weight is greater than the proportion of the aromatic monosulfonic acid in percent by weight, based on the composition.

9. The composition according to claim 8, wherein the at least one α-amino acid derivative is creatinine.

10. The composition according to claim 8, wherein the at least one α-amino acid derivative and the at least one aromatic monosulfonic acid are present in a percent by weight ratio of 10:1 to 1.1:1.

11. The composition according to claim 8, wherein the aromatic monosulfonic acid is selected from the group of 2-arylbenzimidazole-5-sulfonic acid, 2-hydroxy-4-methoxybenzophenone-5-sulfonic acid and sulfonic acid derivatives of 3-benzylidenecamphor.

12. A process for the preparation of a composition according to claim 8, wherein at least one α-amino acid derivative that is 2-pyrrolidone-5-carboxylic acid, creatinine, creatine, hydroxyectoine is mixed with at least one sparingly soluble substance and a vehicle which is suitable for topical applications.

13. A mixture comprising at least one α-amino acid derivative that is 2-pyrrolidone-5-carboxylic acid, creatinine, creatine, hydroxyectoine or a salt or hydrate thereof and at least one sparingly soluble substance which is an organic acid.

14. The mixture according to claim 13, wherein the mixture is a solid mixture.

15. The mixture according to claim 13, wherein the at least one α-amino acid derivative and the at least one sparingly soluble substance are present in a percent by weight ratio of 10:1 to 1.1:1.

16. The mixture according to claim 13, wherein the mixture comprises 90% by weight to 11% by weight of at least one α-amino acid derivative and 45% by weight to 10% by weight of at least one sparingly soluble substance.

17. The mixture according to claim 13, wherein the at least one sparingly soluble organic acid is an aromatic monosulfonic acid.

18. The mixture according to claim 13, wherein a release agent is present.

19. The process for the preparation of a mixture according to claim 13, wherein an α-amino acid derivative is dissolved in a suitable solvent, the sparingly soluble substance and optionally a release agent are introduced, and the solvent is removed.

20. A method for improving the solubility of phenylbenzimidazolesulfonic acid comprising admixing a water or aqueous solution of phenylbenzimidazolesulfonic acid with least one α-amino acid derivative that is 2-pyrrolidone-5-carboxylic acid, creatinine, creatine, hydroxyectoine or a salt or hydrate thereof
or
adding a mixture of phenylbenzimidazolesulfonic acid and at least one α-amino acid derivative that is 2-pyrrolidone-5-carboxylic acid, creatinine, creatine, hydroxyectoine or a salt or hydrate thereof to water or an aqueous solution.

21. A method for improving the solubility of a sparingly soluble substance which is an organic acid comprising admixing a water or aqueous solution of a sparingly soluble substance which is an organic acid with creatinine or a salt or hydrate thereof
or
adding a mixture of a sparingly soluble substance which is an organic acid and creatinine to water or an aqueous solution.

22. A method for preparing a cosmetic composition, pharmaceutical composition, medical composition or food composition comprising admixing a mixture according to claim 13, with a cosmetic composition, pharmaceutical composition, dermatological composition or food composition.

23. A mixture according to claim 13, wherein the sparingly soluble substance is benzoic acid, benzylic acid, formic acid, propionic acid, salicylic acid or sorbic acid.

24. A mixture according to claim 23, wherein the sparingly soluble substance is benzoic acid, benzylic acid or sorbic acid.

* * * * *